United States Patent
Bosch et al.

(10) Patent No.: US 7,754,921 B2
(45) Date of Patent: Jul. 13, 2010

(54) SHAPED BODY COMPRISING AN ALUMINOSILICATE AND ALUMINIUM OXIDE AND PROCESS FOR THE CONTINUOUS PREPARATION OF METHYLAMINES

(75) Inventors: Marco Bosch, Mannheim (DE); Roderich Röttger, Mannheim (DE); Jan Eberhardt, Mannheim (DE); Thomas Krug, Worms (DE); Manfred Julius, Limburgerhof (DE); Karl-Heinz Roß, Grünstadt (DE); Theodor Weber, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 238 days.

(21) Appl. No.: 12/088,743

(22) PCT Filed: Sep. 21, 2006

(86) PCT No.: PCT/EP2006/066575

§ 371 (c)(1),
(2), (4) Date: Apr. 23, 2008

(87) PCT Pub. No.: WO2007/036478

PCT Pub. Date: Apr. 5, 2007

(65) Prior Publication Data
US 2008/0255390 A1  Oct. 16, 2008

(30) Foreign Application Priority Data
Sep. 29, 2005 (DE) .............. 10 2005 046 815
Oct. 18, 2005 (DE) .............. 10 2005 049 746
Jun. 1, 2006 (EP) .................. 06114868

(51) Int. Cl.
*C07C 209/16* (2006.01)
*B01J 29/00* (2006.01)

(52) U.S. Cl. ............. 564/479; 564/474; 564/480; 502/60

(58) Field of Classification Search ......... 564/474, 564/479
See application file for complete search history.

(56) References Cited

U.S. PATENT DOCUMENTS

| 1,875,747 | A |   | 9/1932 | Martin et al. |
|---|---|---|---|---|
| 3,387,032 | A |   | 6/1968 | Leonard |
| 5,399,769 | A | * | 3/1995 | Wilhelm et al. .......... 564/480 |
| 6,294,633 | B1 | * | 9/2001 | Hidaka et al. ........... 564/479 |
| 6,733,657 | B2 |   | 5/2004 | Benazzi et al. |
| 2002/0160911 | A1 |  | 10/2002 | Benazzi et al. |
| 2006/0116517 | A1 |  | 6/2006 | Bosch et al. |

FOREIGN PATENT DOCUMENTS

| CN | 1704165 A | 12/2005 |
|---|---|---|
| DE | 1543731 | 9/1959 |
| DE | 108275 | 9/1974 |
| DE | 149213 | 7/1981 |
| DE | 266096 | 3/1989 |
| DE | 102004062718 | 6/2006 |
| EP | 0062428 | 10/1982 |
| EP | 0064380 | 11/1982 |
| SU | 1766450 | 10/1992 |
| SU | 1766499 | 10/1992 |
| WO | WO 02/055192 | 7/2002 |
| WO | WO-2004/108280 | 12/2004 |
| WO | WO-2005/123685 | 12/2005 |
| WO | WO-2006/032782 | 3/2006 |

OTHER PUBLICATIONS

Catalysis Today, 1997, 37, pp. 71-102, "Methylamines synthesis: A review".
Ind. Eng. Chem. Res., 2004, 43, pp. 5123-5132, "Transalkylation of Metehyiamines: Kinetics and Industrial Simulation".
"Alkylamines" PEP-Report No. 138, 1961 SRI International. Menlo Park, California.
Ullmann's Encyclopedia of Industrial Chemistry. 5th Edition, A16, pp. 535-541, (1990).

* cited by examiner

*Primary Examiner*—Brian J Davis
(74) *Attorney, Agent, or Firm*—Connolly Bove Lodge & Hutz LLP

(57) ABSTRACT

Shaped body comprising an aluminosilicate and aluminum oxide, wherein the shaped body has a molar Al/Si ratio in the range from 10 to 30 and an at least bimodal pore distribution for pores having a diameter of greater than 1 nm, with the volume of the pores of the shaped body having a diameter of greater than 10 nm corresponding to at least 40% of the total pore volume of the shaped body, process for producing it and process for the continuous preparation of methylamines by reaction of methanol and/or dimethyl ether with ammonia in the presence of a heterogeneous catalyst, wherein the above-mentioned shaped bodies are used as catalyst.

31 Claims, No Drawings

SHAPED BODY COMPRISING AN ALUMINOSILICATE AND ALUMINIUM OXIDE AND PROCESS FOR THE CONTINUOUS PREPARATION OF METHYLAMINES

The present invention relates to a shaped body comprising an aluminosilicate and aluminum oxide, a process for producing it and a process for the continuous preparation of methylamines by reaction of methanol and/or dimethyl ether with ammonia.

Monomethylamine (MMA) is an intermediate which is used in the synthesis of pharmaceuticals (e.g. theophyllin), pesticides (carbaryl, metham sodium, carbofuran), surfactants, photographic developers, explosives and solvents such as N-methyl-2-pyrrolidone (NMP).

Dimethylamine (DMA) is likewise a synthetic intermediate. Examples of products based on dimethylamine are fungicides and vulcanization accelerators (zinc bis(dimethyldithiocarbamate)) (ziram), tetramethylthioperoxydicarbonic diamide (TMTD), tetramethylthiocarbonic diamide (MTMT), the fuel 1,1-dimethylhydrazine, various pharmaceuticals, monomers such as dimethylaminoethyl methacrylate, solvents (N,N-dimethylformamide, N,N-dimethylacetamide), catalysts [e.g. 2,4,6-bis[(dimethylamino)methyl]phenol (DMP 30)], the insecticide dimefax, surfactants and ion-exchange resins.

Trimethylamine (TMA) is used in the preparation of choline salts, cationic starches, disinfectants, flotation aids, sweeteners and ion-exchange resins.

Monomethylamine (MMA), dimethylamine (DMA) and trimethylamine (TMA) are synthesized from ammonia and methanol in the gas phase, e.g. over amorphous alumina or silica-alumina (mixed forms of aluminum oxide and silicon oxide), at pressures of from 10 to 50 bar. When relatively high temperatures (350 to 475° C.) are employed, the thermodynamic equilibrium is established or is approximately reached over these heterogeneous catalysts when the residence time in the reactor at the given pressure and given feed temperature is sufficient (cf.: Catalysis Today, 1997, 37, pages 71-102).

In the alkylation of ammonia, monomethylamine (MMA) and/or dimethylamine (DMA) with methanol (=amination reaction), the reaction rate increases in the order $NH_3 < MMA < DMA$. Accordingly, the proportion of TMA over the amorphous "equilibrium catalysts" in a single pass is, based on the sum of MMA, DMA and TMA, from 35 to 75 percent by weight. The product distribution is dependent on the temperature and on the N/C ratio (cf.: Ind. Eng. Chem. Res. 2004, 43, pages 5123-5132).

The worldwide consumption of trimethylamine, based on the total amount of methylamines, is less than 20 percent by weight (cf.: Ullmann's Encyclopedia of Industrial Chemistry, 5th edition, A16, pages 535-541). It is therefore necessary to increase the proportion of DMA and MMA in the reaction mixture.

This is achieved by recirculation of TMA and ammonia to the catalyst; in the synthesis the TMA is converted into a mixture of MMA, DMA and TMA (=transalkylation reaction). The process for preparing methylamines from methanol and ammonia, in which the amination and transalkylation reactions are combined, is referred to as the Leonard process (cf.: U.S. Pat. No. 3,387,032, "Alkylamines" PEP Report No. 138, 1981, (SRI International, Menlo Park, Calif.) and Hydrocarbon Process 1979, 58, page 194ff). The recirculation enables the product mix to be set according to requirements; a typical example is a mixture consisting of 34% by weight of MMA, 46% by weight of DMA and 20% by weight of TMA ("Alkylamines" PEP Report No. 138, 1981).

U.S. Pat. No. 1,875,747 (Martin et al.) describes the preparation of methylamines from $NH_3$ and MeOH over aluminosilicate catalysts at temperatures of from 300 to 500° C. The aluminosilicate can be used as a synthetic solid or in the form of a clay mineral.

EP-A-64 380 (DuPont) describes a catalyst which is obtained by treatment of an aluminosilicate with the hydroxide salts of sodium, potassium, lithium, barium or strontium, with the proportion of Na, K, Li, Ba or Sr being in the range from 0.1 to 6% by weight. The use of the catalyst for preparing methylamines from methanol and ammonia, with the proportion of monomethylamine (MMA) being able to be adjusted by increasing the proportion of alkali metal and/or alkaline earth metal, is likewise mentioned.

DD-A-266 096 (VEB Leuna) describes a process for preparing methylamines over an $SiO_2$—$Al_2O_3$ dehydration catalyst. Here, an $Al_2O_3$ or $Al_2O_3/SiO_2$ support is sprayed with an $HNO_3$-comprising suspension of finely milled boehmite and kaolin in water in a fluidized bed and the spherical catalyst after thermal activation at from 400 to 600° C. has a bulk density of from 0.5 to 0.6 kg/l, an $Al_2O_3$ content of from von 70 to 80% and a pore volume of from 0.75 to 0.85 ml/g, with the pore volume in the range of pores having diameters below 15 nm having to be at least 0.3 ml/g and that in the range of pores having diameters above 15 nm having to be at least 0.4 ml/g and among these the pore volume in the range of pores having a diameter above 100 nm having to be at least 0.2 ml/g. The catalysts according to the invention are said to have a 20% longer operating life and, after removal from the reactor, have a lower degree of carbon-comprising deposits and broken shaped bodies. The proportion of $Al_2O_3$ in the range from 70 to 80% corresponds to a molar Al/Si ratio of from 2.7 to 4.7.

DD-A-149 213 (VEB Leuna) discloses a process for preparing methylamines over dehydrating catalysts comprising active aluminum oxide. Here, use is made of a catalyst which is produced on the basis of kaolin and pseudoboehmite and comprises from 12 to 18% by weight of silicon dioxide in addition to aluminum oxide and has a total pore volume of greater than 0.5 ml/g, with the proportion of pores having a diameter of less than 4 nm being at least 30% and that of pores larger than 15 nm being not more than 10% and the particle size or wall thickness being less than 4 mm. The catalyst is said to have been able to be operated for 13 months without significant deactivation [C(MeOH)>99%] and the deposit on the catalyst removed from the reactor comprised about 1.2% by weight of carbon. The proportion of $SiO_2$ in the range from 12 to 18% corresponds to a molar Al/Si ratio of from 5.4 to 8.6.

EP-A-62 428 (=U.S. Pat. No. 4,370,503) describes the use of a catalyst comprising from 88 to 99% by weight of alumina and from 1 to 13% by weight of silica for the preparation of methylamines from methanol or dimethyl ether and ammonia. The weight distributions of silica and alumina correspond to a molar Al/Si ratio of from 7.9 to 116.7. The catalyst is usually in the form of a pellet having a diameter and/or length of from 3 to 13 mm. The pore volume of the pellet is in the range from 0.2 to 0.8 ml/g, and the BET surface area is from 100 to 250 m²/g.

DD-A-108 275 (Becker et al.) describes a process for preparing methylamines over fixed-bed catalysts comprising aluminum oxide and/or aluminosilicates, with the catalyst being used in the form of a hollow rod whose total diameter is from 3 to 10 mm and whose internal diameter is from 1 to 5 mm and which has at least 30% of pores having a diameter greater than 100 Å, a surface area of at least 130 m$^2$/g and an acidity of not more than 2.0×10$^{-5}$ mol of NH$_3$/g. Compared to the solid rod, use of the high rod is said to have given a 41% lower pressure drop, resulted in reduced formation of secondary components, enabled the deposition of low-hydrogen compounds to be reduced and enabled the operating life of the catalyst to be increased by 30%.

SU-A1-1766 499 (Chem. Abstr. 120: 57149) describes the production of a silica-alumina catalyst. The improvement over the prior art comprises, according to the description, the use of Al(OH)$_3$ instead of pseudoboehmite, reduction of the kaolin to aluminum hydroxide mass ratio from 50 to 10, addition of regrind in catalyst production and peptization of the mixture by means of HNO$_3$ followed by treatment with an ammoniacal solution before extrusion. The measures are said to enable the activity to be increased and the mechanical properties of the shaped bodies to be improved.

SU-A1-1766 500 (Chem. Abstr. 120: 57148) builds on SU-A1-1766 499 and describes the advantageous use of formic acid instead of nitric acid for the peptization of the extrusion composition.

DE-A-1 543 731 (Leonard) teaches a process for preparing amines by reacting ammonia with alcohols, ethers and mixtures thereof in the gaseous phase and in the presence of catalysts, in which the catalyst is based on silica gel onto which active aluminum oxide and traces of metal salt promoters have been applied. The catalyst is partially deactivated by treatment with steam at 1-50 atmospheres before use. The catalyst usually comprises from 12 to 13% by weight of Al$_2$O$_3$. The steam treatment reduces the total surface area of the catalyst to 90±20 m$^2$/g and results in a pore volume of 0.34±0.10 ml/g and a pore diameter of 74±10 Å. It is said that the deactivation of the aluminosilicate and the application of silver, rhenium, molybdenum and cobalt salts was able to increase the proportion of DMA in the reaction mixture from 32-35% by weight to >50% by weight.

According to the abovementioned PEP reports of 1981, which reports on the preparation of alkylamines, especially methylamines, the operating life of an aluminosilicate catalyst is about 1.5 years. ("Alkylamines", M. Arné, Process Economics Program Report No. 138, 1981, California, USA, pages 19-41).

The operating life of the aluminosilicate catalysts described in the prior art is a maximum of 2 years.

The German patent application No. 102004062718.5 of Dec. 21, 2004 (BASF AG) relates to a process for preparing methylamines from methanol in the presence of an acidic, shape-selective molecular sieve and in the presence of hydrogen. For the development of a catalyst for the methylamine process, it is desirable for the catalyst to be active both for the amination reaction and for the transalkylation reaction under the prescribed reaction conditions. For the purposes of the present invention, the term amination reaction refers to the reaction of ammonia, MMA and/or DMA with methanol and/or dimethyl ether with elimination of water. Transalkylation is the reaction of MMA, DMA and/or TMA with itself or with ammonia (see: Ullman's Encyclopedia of Industrial Chemistry, 5th edition, 1996, vol. A16, pages 535-541 and Catalysis Today 1997, 37, pages 71-102).

Both reactions are acid-catalyzed, so that the acidity of the catalyst, which is determined by the density and strength of the Brönsted- and/or Lewis-acid sites, is of critical importance (cf.: Ind. Eng. Chem. Res. 2004, 43, pages 5123-5132). The acidity of the catalyst should, according to the invention, be optimized so that activation of the starting materials by complex formation with the active site is possible but the complexes are not so stable that coke and/or coke precursors form or the active sites become deactivated. One possible way of influencing the acidity of the catalyst is to adjust the molar Al/Si-ratio.

If the acidity of the catalyst is adjusted, the residence time of the starting materials and products in the shaped catalyst bodies should be optimized so that sufficient diffusion of the starting materials and products from and to the active sites and of the reaction medium into and out of the pores of the catalyst is possible under the given reaction conditions. Since the silica/alumina catalysts are generally not microporous, optimization of the porosity of the catalyst means optimization of the macropores (pore diameter >25 nm) and/or mesopores (pore diameter 1-25 nm).

For the catalyst to be used on a production scale, the geometry of the shaped bodies should be selected so that the pressure drop in the reactor is very low. In addition, the shaped bodies should be so mechanically stable under the given reaction conditions that fill heights of, for example, up to 40 m are possible and the formation of attrited material during the reaction is minimized.

It was thus an object of the present invention to discover an improved catalyst and an improved economical process for preparing methylamines. In particular, the process should ensure an operating life of the catalyst of more than 2 years at a high methanol conversion (e.g. >95%).

We have accordingly found a shaped body comprising an aluminosilicate and aluminum oxide, wherein the shaped body has a molar Al/Si ratio in the range from 10 to 30 and an at least bimodal pore distribution for pores having a diameter of greater than 1 nm, with the volume of the pores of the shaped body having a diameter of greater than 10 nm corresponding to at least 40% of the total pore volume of the shaped body.

The pore volumes are determined by means of Hg porosimetry in accordance with DIN 66134.

Furthermore, we have found a process for producing the abovementioned shaped body, which comprises the steps
(I) preparation of a mixture comprising the aluminosilicate, in particular a clay, the aluminum oxide as binder, a pasting agent and a solvent,
(II) mixing and densification of the mixture,
(III) shaping of the densified mixture to give a shaped body,
(IV) drying of the shaped body and
(V) calcination of the dried shaped body, and a process for the continuous preparation of methylamines by reaction of methanol and/or dimethyl ether with ammonia in the presence of a heterogeneous catalyst, wherein the abovementioned shaped bodies are used as catalyst.

In the process of the invention, the operating life of the catalyst of the invention is more than 3 years, in particular more than 4 years, and is, for example, in the time range from 3.5 to 6 years.

With regard to the production and properties of the inventive shaped bodies which are used as catalyst in the process of the invention, the following may be said:

The Aluminosilicate (Step I)

As aluminosilicate, preference is given to using clays and particularly preferably sheet silicates from the kaolin group (cf.: Ullman's Encyclopedia of Industrial Chemistry, 6th edition, 2000 electronic edition, chapter 2, and Lehrbuch der Anorganischen Chemie, A. F. Holleman, E. Wiberg, de Gruyter-Verlag, Berlin, 91st-100th edition, 1985, pp. 771-776). Very particular preference is given to using kaolinite {formula: Al$_2$(OH)$_4$[Si$_2$O$_5$]}.

Kaolinite is a major constituent of kaolin which is obtained, inter alia, from deposits in Georgia, England, the USA, Brazil, Germany, the Czech Republic, Spain, Russia and Australia (cf.: Ullman's Encyclopedia of Industrial Chemistry, 6th edition, 2000 electronic edition, chapter 3.1). Natural kaolin comprises kaolinite together with small amounts of feldspars, mica and quartz and can be purified by the method; known to those skilled in the art; namely, in particular, the "dry process" and "wet process" mentioned in Ullman's Encyclopedia of Industrial Chemistry, 6th edition, 2000 electronic edition, chapter 4.1. Kaolinite can be obtained synthetically from polysilicic acid and aluminum hydroxide by hydrothermal synthesis at pH<7.

The clay, preferably the kaolin and particularly preferably the kaolinite, preferably comprises traces of titanium, iron, sodium and potassium. The proportions of these elements are preferably from 0.1 to 1.0% by weight of titanium, from 0.1 to 1.0% by weight of iron, from 0.1 to 5.0% by weight of potassium and from 0.1 to 5.0% by weight of sodium.

The proportion of aluminosilicate, in particular clay, preferably kaolin and particularly preferably kaolinite, in the finished catalyst extrudate is from 1 to 30% by weight, preferably from 2 to 20% by weight and particularly preferably from 5 to 15% by weight.

The Aluminum Oxide Binder (Step I)

Binders used are oxides of alumina and particularly preferably $\gamma$-$Al_2O_3$.

Aluminum hydroxide and/or aluminum oxide/hydroxide is added to the mixture in step I as precursor of the aluminum oxide. As aluminum hydroxide, it is possible to use either synthetic $Al(OH)_3$ or natural hydrargillite [$\gamma$-$Al(OH)_3$]. As aluminum oxide/hydroxide [$\gamma$-$Al(O)OH$], preference is given to using boehmite and/or pseudoboehmite.

In a particular embodiment, a mixture of aluminum hydroxide and/or aluminum oxide/hydroxide and $\gamma$-$Al_2O_3$ is used as precursor.

In the calcination step V, in particular at least 80% of the aluminum hydroxide and/or aluminum oxide/hydroxide used is converted into $\gamma$-$Al_2O_3$.

The proportion of binder in the finished shaped body, e.g. extrudate, is in particular at least 50% by weight and is preferably in the range from 50 to 99% by weight, particularly preferably from 75 to 95% by weight.

The Solvent (Step I)

As solvent, which can also be a diluent, use is made, in particular, of water.

Either Brönsted acids or Brönsted bases can be added to the water.

Suitable Brönsted acids are, for example, hydrochloric acid, sulfuric acid, phosphoric acid, nitric acid or carboxylic acids, dicarboxylic acids or oligocarboxylic or polycarboxylic acids, for example nitrilotriacetic acid, sulfosalicylic acid or ethylenediaminetetraacetic acid.

Preference is given to using formic acid or nitric acid as Brönsted acid.

Suitable Brönsted bases are primary, seconday and tertiary alkylamines, ammonia and also rare earth metal hydroxides, alkalimetal hydroxides and alkaline earth metal hydroxides.

Preference is given to using ammonia as Brönsted base.

The proportion of Brönsted acids and/or Brönsted bases in the solvent (e.g. water) is, in particular, from 0.5 to 99% by weight, preferably from 1 to 50% by weight, particularly preferably from 5 to 25% by weight.

The addition of the solvent results in the mixture having the correct consistency for further processing in the shaping step. The proportion of solvent is preferably in the range from 0.5 to 80% by weight, more preferably in the range from 0.8 to 50% by weight, more preferably in the range from 1 to 40% by weight and particularly preferably in the range from 1.5 to 30% by weight, in each case based on the total mass of the mixture prepared in step I.

In a particular embodiment, the mixture is firstly treated with a solution of a Brönsted acid (e.g. formic acid) and then with a solution of a Brönsted base (e.g. $NH_3$).

The Pasting Agent (Step I)

In the preparation of the mixture in (I), at least one pasting agent (=Organic additive) is added.

As pasting agents, it is possible to use all compounds suitable for this purpose. These are preferably organic, in particular hydrophilic, polymers such as cellulose, cellulose derivatives, for example methylcellulose, starch, for example potato starch, polyacrylates, polymethacrylates, polyvinyl alcohol, polyvinylpyrrolidone (PVP), polyisobutene (PIB) or polytetrahydrofuran (PTHF).

In particular, compounds which also act as pore formers can be used as pasting agents.

In a particularly preferred embodiment of the process of the invention, the pasting agent is, as described below, removed to an extent of at least 90% by weight by calcination in step V.

The addition of the pasting agent results in the mixture having the correct consistency for further processing in the shaping step. The proportion of pasting agent is preferably in the range from 0.5 to 80% by weight, more preferably in the range from 1 to 50% by weight, more preferably in the range from 2 to 40% by weight, and particularly preferably in the range from 3 to 30% by weight, in each case based on the total mass of the mixture prepared in step 1.

Pore Formers (Optional, Step I)

The mixture of binder, aluminosilicate, pasting agent and solvent prepared in I can be admixed with at least one further compound for further processing and for formation of a plastic mass. Preference is here given to, inter alia, pore formers.

As pore formers in the process of the invention, it is possible to use all compounds which provide a particular pore size, a particular pore size distribution and/or particular pore volumes in the finished shaped body.

Pore formers used in the process of the invention are preferably polymers which can be dispersed, suspended and/or emulsified in water or in aqueous solvent mixtures. Preferred polymers are polymeric vinyl compounds such as polyalkylene oxides, e.g. polyethylene oxides, polystyrene, polyacrylates, polymethacrylates, polyolefins, polyamides and polyesters, carbohydrates such as cellulose or cellulose derivatives, for example methylcellulose, or sugars or natural fibers. Further suitable pore formers are paper pulp or graphite.

Preference is also given to acidic organic compounds which can be removed by calcination in step V, as described below. Mention may here be made of carboxylic acids, in particular $C_{1-8}$-carboxylic acids such as formic acid, oxalic acid and/or citric acid. It is also possible to use two or more of these acidic compounds.

If pore formers are added in the preparation of the mixture in step I, the content of pore formers in the mixture prepared in (I) is preferably in the range from 0.5 to 80% by weight, very preferably in the range from 1 to 50% by weight and particularly preferably in the range from 2 to 30% by weight, in each case based on the total mass in the mixture prepared in (I).

Should it be desirable for the pore size distribution to be achieved, a mixture of two or more pore formers can also be used.

In a particularly preferred embodiment of the process of the invention, the pore formers are, as described below, removed to an extent of at least 90% by weight by calcination in step V to give the porous shaped body.

Mixing and Densification (Step II)

After preparation of the mixture in (I), the mixture is homogenized, e.g. for a period in the range from 10 to 180 minutes. Particular preference is given to using, inter alia, kneaders, pan mills or extruders for homogenization. On a relatively small scale, the mixture is preferably kneaded. On a larger industrial scale, pan milling is preferably used for homogenization.

The homogenization is preferably carried out at temperatures in the range from about 10° C. to the boiling point of the solvent and under atmospheric pressure or slightly superatmospheric pressure. At least one of the compounds described above as pasting agent or pore former can then be added if appropriate. The mixture obtained in this way is homogenized, preferably kneaded, until an extrudable plastic mass has been formed.

The homogenized mixture is shaped in a subsequent step.

Shaping of the Densified Mixture to Give a Shaped Body (Step III)

This step is preferably carried out using processes in which shaping is effected by extrusion in customary extruders, for example to give extrudates having a diameter of preferably from 1 to 20 mm and particularly preferably from 2 to 15 mm, e.g. from 1 to 10 or from 2 to 5 mm. Such extrusion apparatuses are described, for example, in Ullmann's Enzyklopädie der Technischen Chemie, 4th edition, volume 2, p. 295 ff., 1972. Apart from the use of a screw extruder, preference is likewise given to using a ram extruder for shaping.

However, all known and/or suitable kneading and shaping apparatuses or methods can in principle be used for shaping. Mention may be made, inter alia, of the following:

(i) briquetting, i.e. mechanical pressing with or without addition of additional binder material;
(ii) pelletization, i.e. compaction by means of circular and/or rotating movements;
(iii) sintering, i.e. the material to be shaped is subjected to a thermal treatment.

For example, the shaping method can be selected from the following group, with combinations of at least two of these methods being explicitly included: briquetting by pressing by means of a punch, roller pressing, annular roller pressing, briquetting without binder; pelletization, fusion, spinning techniques, deposition, foaming, spray drying; firing in shaft furnaces, convection furnaces, moving grate, rotary tube furnaces, pan milling.

Compaction can take place at ambient pressure or at a pressure above ambient pressure, for example in a pressure range from 1 bar to several hundred bar. Furthermore, compaction can take place at ambient temperature or at a temperature above ambient temperature, for example in a temperature range from 20 to 300° C. If drying and/or firing is part of the shaping step, temperatures up to 1500° C. can be employed. Finally, compaction can take place in the ambient atmosphere or in a controlled atmosphere. Controlled atmospheres are, for example, protective gas atmospheres, reducing or oxidizing atmospheres.

The shape of the shaped bodies produced according to the invention can be selected freely. In particular, possible shapes include, inter alia, spheres, oval shapes, cylinders, cylindrical extrudates or pellets.

The length:diameter ratio of the extrudates is, in particular, at least 1, preferably in the range from >1 to 20, particularly preferably in the range from 2 to 10.

Drying of the Shaped Body (Step IV)

For the purposes of the present invention, step (III) is preferably followed by at least one drying step. This at least one drying step is carried out at temperatures in the range from preferably 80 to 160° C., in particular from 90 to 145° C. and particularly preferably from 100 to 130° C., with the drying time preferably being 6 hours or more, for example in the range from 6 to 24 hours. However, depending on the moisture content of the material to be dried, shorter drying times such as approximately 1, 2, 3, 4 or 5 hours are also possible.

Before and/or after the drying step, the extrudate which is preferably obtained can, for example, be comminuted. This preferably gives granules or crushed material having a particle size in the range from 0.1 to 5 mm, in particular from 0.5 to 2 mm.

Calcination of the Shaped Body (Step V)

Step (IV) is followed by at least one calcination step. The calcination is carried out at temperatures in the range from preferably 350 to 750° C. and in particular from 450 to 700° C.

Calcination can be carried out under any suitable gas atmosphere, with air and/or lean air being preferred.

The calcination (V) can also be carried out in the presence of hydrogen, nitrogen, helium, argon and/or steam or mixtures thereof.

Furthermore, the calcination is preferably carried out in a muffle furnace, a rotary tube furnace or a belt calcination furnace, with the calcination time preferably being 1 hour or more, for example in the range from 1 to 24 hours or in the range from 3 to 12 hours. Accordingly, the shaped body can, for example, be calcined once, twice or more often for at least 1 hour in each case, for example in the range from 3 to 12 hours in each case, in the process of the invention, with the temperatures being able to remain constant or be changed continuously or discontinuously during the calcination step. If calcination is carried out twice or more often, the calcination temperatures in the individual steps can be different or identical.

After the calcination step, the calcined material can, for example, be comminuted. This preferably gives granules or crushed material having a particle size in the range from 0.1 to 5 mm, in particular from 0.5 to 2 mm.

The shaped bodies obtained have hardnesses which are preferably in the range from 2 to 200 N (newton), particularly preferably in the range from 5 to 150 N and very particularly preferably at least 10 N, e.g. in the range from >10 to 100 N.

The above-described hardness was, for the purposes of the present invention, determined on a Zwick model BZ2.5/TS1S apparatus using an initial force of 0.5 N, a preliminary advance rate of 10 mm/min and a subsequent test speed of 1.6 mm/min. The apparatus has a fixed rotary plate and a freely movable punch having a built-in cutter having a thickness of 0.3 mm. The movable punch with the cutter was connected to a load cell for force measurement and during the measurement moved toward the fixed rotary plate on which the shaped catalyst body to be examined was located. The test apparatus was controlled via a computer which recorded and evaluated the measured results. The values achieved represent the mean of the measurement on in each case at least 10 shaped catalyst bodies.

The shaped bodies obtained preferably have a molar Al/Si ratio in the range from 10 to 35, in particular in the range from 11 to 26. For example, the molar Al/Si ratio is in the range from 12 to 25, in particular from 14 to 23.

The figures given for the molar Al/Si ratio in the shaped body are based on the total content of Al and Si.

The acidity of the shaped bodies is a function of the molar Al/Si ratio in the shaped body. In the molar Al/Si ratio range from 10 to 30, the acidity increases with decreasing molar Al/Si ratio.

The acidity is determined by means of FT-IR spectroscopy. Here, the intensity of the sorption bands at $\nu=1490\pm2$ cm$^{-1}$ and/or $1440\pm2$ cm$^{-1}$ of samples (compacts) exposed to pyridine gas is measured at 80° C. and 1.0 mbar using a method analogous to that described in Journal of Catalysis 1963, 2, pages 371-379. The intensity of the bands is reported as extinction based on the layer thickness of the compacts measured as integral extinction units (IEU) per μm of layer thickness.

In the case of the sorption band at $\nu=1490\pm2$ cm$^{-1}$, the value of IEU/μm at a pyridine partial pressure of 1.0 mbar is preferably in the range from 0.001 to 0.015 and particularly preferably in the range from 0.003 to 0.010.

In the case of the sorption band at $\nu=1440\pm2$ cm$^{-1}$, the value of IEU/μm at a pyridine partial pressure of 1.0 mbar is preferably in the range from 0.020 to 0.100 and particularly preferably in the range from 0.025 to 0.060.

The sorption bands in the FT-IR spectrum at $\nu=1490\pm2$ cm$^{-1}$ and $1440\pm2$ cm$^{-1}$ of the samples exposed to pyridine gas correspond to the coordination of pyridine by Lewis acid sites (see Journal of Catalysis 1963, 2, pages 371-379, Catalysis and Zeolites (Eds. J. Weitkamp, L. Puppe), 1999, Springer Verlag, Berlin, chapter 4.1.5.1.3, pages 224-226, and Catalysis Today 2001, 68, pages 263-381). The sorption band at $\nu=1540\pm2$ cm$^{-1}$ typical of Brönsted acid sites in the IR spectrum of a sample exposed to pyridine gas is not observed in the case of the shaped aluminosilicate bodies of the invention or used according to the invention.

The specific surface area of the shaped bodies obtained, determined in accordance with DIN 66131 (BET), is preferably at least 50 m$^2$/g and particularly preferably at least 100 m$^2$/g. For example, the specific surface area is in the range from 50 to 250 m$^2$/g and in particular in the range from 100 to 200 m$^2$/g.

The pore volume of the shaped bodies obtained, determined in accordance with DIN 66134 (Hg-porosymmetry), is preferably at least 0.4 ml/g, particularly preferably at least 0.6 ml/g. For example, the pore volume is in the range from 0.4 to 1.5 ml/g and in particular in the range form 0.6 to 1.0 ml/g.

The pores having a diameter of >1 nm of the shaped bodies obtained, determined in accordance with DIN 66134 (Hg porosimetry), have a multimodal, at least bimodal distribution, preferably a bimodal distribution, with the proportion of pores having a diameter of >10 nm being at least 40%, preferably at least 50%, of the total pore volume and, for example, being in the range from 40 to 60%.

The shaped bodies preferably comprise traces of titanium, iron, sodium and potassium. The proportion of these elements is preferably from 0.01 to 0.35% by weight of titanium, from 0.01 to 0.35% by weight of iron, from 0.01 to 1.75% by weight of potassium and from 0.01 to 1.75% by weight of sodium, in each case based on the weight of the shaped body.

Preparation of Methylamines Over the Catalyst of the Invention:

The preparation of methylamines over the catalyst of the invention is effected by reaction of ammonia and methanol and/or dimethyl ether in the gas phase at elevated pressure and elevated temperature. If desired, water and/or monomethylamine and/or dimethylamine and/or trimethylamine can also be added to the feed for the reaction or be comprised therein.

The space velocity over the catalyst is expressed as mass of carbon-comprising compounds in the feed, calculated as methanol, per catalyst volume (l=liter) and time. The space velocity over the catalyst is preferably in the range from 0.1 to 2.0 kg (methanol)/l(catalyst)/h, in particular in the range from 0.2 to 1.5 kg/l/h, very particularly preferably in the range from 0.4 to 1.0 kg/l/h.

The molar N/C ratio based on the sum of the starting materials is preferably in the range from 0.6 to 4.0, in particular from 0.8 to 2.5, very particularly preferably from 1.0 to 2.0.

The reaction is preferably carried out at a temperature in the range from 250 to 500° C., particularly preferably from 300 to 475° C., very particularly preferably from 350 to 450° C.

The absolute pressure in the reaction is preferably in the range from 5 to 50 bar, particularly preferably from 10 to 30 bar, in particular from 15 to 25 bar.

The methanol conversion (Conv) is preferably >85%, particularly preferably from 90% to 99%, in particular from 95% to 99%.

The selectivity (=S) of the reaction to monomethylamine, dimethylamine and trimethylamine is preferably >90%, particularly preferably >95%.

The shaped bodies used in the process of the invention preferably form a fixed catalyst bed, e.g. produced by pouring.

The reaction is preferably carried out in an adiabatically operated shaft reactor.

In a particular embodiment of the process of the invention for preparing methylamines, the shaped bodies of the invention are used as catalyst and form a fixed bed comprising two, three, four or more, preferably two, different types of shaped bodies which differ in terms of their acidity.

The at least two different types of shaped bodies (shaped body type A, shaped body type B, . . . ) can be arranged in the form of a homogeneous mixture or in the form of zones which are each made up of a different type of shaped body. When two zones are installed, the shaped body type (A) having the smaller Al/Si ratio is preferably installed downstream of the shaped body type (B) having a larger Al/Si ratio.

In the case of two different types of shaped bodies in the fixed catalyst bed, the weight ratio of the shaped body types A and B (A:B) in the bed is in the range from 10:90 to 90:10, preferably from 20:80 to 80:20 and particularly preferably from 30:70 to 70:30.

The difference between the molar Al/Si ratio of the shaped body types A and B is not more than 20 and is preferably in the range from $\geq 2$ to $\leq 20$, particularly preferably in the range from $\geq 3$ to $\leq 10$.

The work-up of the output from the reactor can be carried out in a manner based on methods known to those skilled in the art, e.g. as described in DD-125 533 (VEB Leuna-Werke).

The process for preparing methylamines using the catalyst of the invention can optionally be carried out in combination with an arrangement comprising a reactor comprising a shape-selective catalyst as described in U.S. Pat. No. 4,485,261 and/or PEP-Review, No. 89-3-4, (SRI International, Menlo Park, Calif.).

In particular embodiments of the invention, the dimethyl ether (DME), trimethylamine (TMA) and/or monomethylamine (MMA) which may be used if appropriate are in each case an appropriate recycle stream from the worked up reaction product of the process.

Regeneration of the Shaped Catalyst Bodies after Use in the Continuous Synthesis of Methylamines:

In a further embodiment of the process of the invention, the catalyst is regenerated after use regardless of its form, e.g. after the activity and/or selectivity has decreased, by a process in which regeneration is effected by targeted burning-off (e.g. at a temperature in the range from 350 to 650° C.) of the deposits responsible for deactivation. This is preferably carried out in an inert gas atmosphere comprising precisely defined amounts of oxygen and/or oxygen-supplying substances. Such a regeneration process is described, inter alia, in WO-A-98/55228 and DE-A1-197 23 949 and particularly for catalysts for preparing methylamines in JP-08 157 428 and EP-A-0118 193, whose relevant disclosure is hereby fully incorporated by reference into the present patent application.

After the regeneration, the activity and/or selectivity of the catalyst are increased compared to the state immediately before regeneration.

The catalyst of the invention to be regenerated is heated, either in the reaction apparatus (reactor) or in an external furnace, at a temperature in the range from 350° C. to 800° C., preferably from 400° C. to 650° C. and in particular from 425° C. to 500° C., in an atmosphere which preferably comprises from 0.1 to about 20 parts by volume of oxygen-supplying substances, particularly preferably from 0.1 to 20 parts by volume of oxygen. The catalyst is preferably heated up at a heating rate of from 0.1° C./min to 20° C./min, preferably from 0.3° C./min to 15° C./min and in particular from 0.5° C./min to 10° C./min. The catalyst is preferably heated up under an inert atmosphere.

During the regeneration, the catalyst is heated to a temperature at which the deposits, usually organic deposits, present there begin to decompose, while at the same time the temperature is regulated via the oxygen content and thus does not rise to such an extent that damage to the catalyst structure or the reactor occurs. The gradual increase in the temperature or the residence at low temperature by setting of the appropriate oxygen content and the appropriate heating power is an essential step for preventing local overheating of the catalyst in the case of high organic loadings of the catalyst to be regenerated. The GHSV (=gas hourly space velocity) of the oxygen-comprising regeneration gas is more than 50 standard liters per liter of catalyst and hour (=Nl/l(catalyst)/h), preferably more than 100 Nl/l/h and particularly preferably in the range from 150 to 1000 Nl/l/h.
(Nl=standard liters=volume at STP).

When the temperature of the offgas stream at the reactor outlet drops to the temperature at the reactor inlet despite increasing amounts of oxygen or oxygen-supplying substances in the gas stream and/or the concentration of oxygen in the output from the reactor increases to the value at the inlet, the burning-off of the organic deposits is complete. The duration of the treatment is preferably from 1 to 72 hours, more preferably from about 2 to about 48 hours and in particular from about 3 to about 24 hours.

The subsequent cooling of the catalyst which has been regenerated in this way is preferably carried out so that cooling does not occur too quickly, since otherwise the mechanical strength of the catalyst can be adversely affected. Cooling is preferably carried out in an inert atmosphere.

After the regeneration by calcination, as described above, has been carried out, it may be necessary to subject the catalyst to washing with water and/or dilute acids such as hydrochloric acid to remove any remaining inorganic contaminants on the catalyst (traces of alkali, etc.) resulting from contamination of the starting materials. The catalyst can subsequently be dried again and/or calcined again.

In a further embodiment of the process of the invention, the at least partly deactivated catalyst is washed with a solvent in the reactor or in an external vessel to remove desired products still adhering to it before it is heated in the regeneration procedure. Washing is carried out so that the desired products adhering to the catalyst can be removed from it but the temperature and pressure are not so high that the usually organic deposits are likewise removed. The catalyst is preferably just rinsed with a suitable solvent. Thus, all solvents in which a respective reaction product dissolves readily are suitable for this washing step. The amount of solvent used and the duration of the washing step are not critical. The washing step can be repeated a number of times and be carried out at elevated temperature. When $CO_2$ is used as solvent, supercritical pressure is preferred; otherwise, the washing step can be carried out under atmospheric pressure or under superatmospheric or supercritical pressure. After the washing step is complete, the catalyst is generally dried. Although the drying step is generally not critical, the drying temperature should not be too far above the boiling point of the solvent used for washing in order to avoid sudden vaporization of the solvent in the pores, since this can lead to damage to the catalyst.

In a preferred embodiment of the preparative process, the continuous process of the invention for the synthesis of methylamines does not have to be interrupted during regeneration of the catalyst of the invention in order to increase the process throughput in this way. This can be achieved by the use of at least two reactors which are connected in parallel and can be operated alternately.

Catalyst regeneration can be carried out so that at least one of the parallel reactors is decoupled from the respective reaction stage and the catalyst comprised in this reactor is regenerated, resulting in at least one reactor always being available for reaction of the starting material or materials in every stage during the course of the continuous process.

EXAMPLES

The BET surface areas ($m^2$/g) and the pore volumes (ml/g) were determined in accordance with the standards DIN 66131 and DIN 66134.

GC Analysis:

The outputs from the reaction were analyzed by means of on-line gas chromatography. Here, the methylamines were separated on a GC column (Varian CP-Volamine) optimized for short-chain amines and a thermal conductivity detector (TCD) was used for detection. The content of unreacted methanol was determined, and the activity of the catalyst was concluded therefrom.

The determination/measurement of the cutting hardness was carried out as described in WO-A-04/108280 (BASF AG) (see also further above in the description).

Example

Production of Catalyst A (According to the Invention)

177 g of gamma-$Al_2O_3$ were mechanically mixed with 222 g of boehmite and 44 g of kaolin and subsequently admixed with 200 g of 4.2% strength formic acid. The composition was then mechanically mixed and admixed with 90 g of aqueous starch solution and 9 g of 25% strength aqueous $NH_3$ solution. The composition obtained in this way was shaped on an extruder to give 4 mm extrudates. The extrudates were dried at 120° C. for 2 hours in a belt dryer and subsequently calcined at 610° C. for 2 hours in a muffle furnace.

The catalyst obtained has a molar Al/Si ratio of 17.3. The proportions of iron, potassium, sodium and titanium are 0.03, 0.21, 0.01 and 0.06% by weight, respectively. The shaped body has a bimodal pore distribution with pore diameters of 7.3 and 11.0 nm. The total pore volume of the pores having a diameter of >1 nm is 0.49 ml/g. The proportion by volume of pores having a diameter of >10 nm is 56%.

The cutting hardness is 68.5 N and the BET surface area is 206 $m^2/g$.

Examples

Continuous Preparation of Methylamines by Reaction of Methanol with Ammonia in the Presence of the Catalyst of the Invention

A)

In an industrial plant for the preparation of methylamines, catalysts according to the invention were used for the synthesis of methylamine from methanol, ammonia and dimethyl ether, monomethylamine and trimethylamine. After a running time of 5 years, the catalyst was replaced. The carbon content of the catalyst removed from the reactor was 1.7% by weight. The plant was subsequently operated for 4 years without replacement of the catalyst. The catalyst removed from the reactor after 4 years had a carbon content of 1.3% by weight. At the time of removal from the reactor, the catalysts each had a good activity (methanol conversions >95%); the catalyst replacement was carried out because engineering work made it necessary for the plant to be shut down.

B)

A catalyst according to the invention was used as 2 mm extrudates and as 4 mm extrudates. The methylamine synthesis was carried out in a single pass without recirculation of reaction components. The experiments were carried out at reaction temperatures of from 350 to 430° C. and space velocities of from 0.4 to 1.2 kg (MeOH)/liter of catalyst/h. The molar N/C ratio was varied in the range from 1.2:1 to 1.8:1. The experiments were carried out in a 1 liter tube reactor having a diameter of 30 mm. The reactor was operated isothermally (electric heating with three heating circuits).

GC Analysis

Separation column: Varian CP-Volamine (WCOT Fused Silica), length: 60 m, internal diameter: 0.32 mm; carrier gas: helium; temperature program: 10 minutes isothermal at 40° C., then increased at 20° C./minute to 250° C., subsequently 5 minutes isothermal at 250° C.

To evaluate the catalyst, a number of experiments were carried out at different temperatures and loadings. When the 4 mm catalyst extrudates were used, no pressure difference in the reactor occurred during the running time of 1300 hours. The catalyst activity continued to be very good. The carbon content of the catalyst removed from the reactor was in the range from 0.4 to 0.6% by weight.

Experimental Results

TABLE 1

Experimental results for the methylamine synthesis at a molar ratio of 1.2:1

| WHSV, molar ratio | Temperature | Running time, absolute, in h | Diameter of extrudates | Conv (MeOH) | MMA % by weight | DMA % by weight | TMA % by weight |
|---|---|---|---|---|---|---|---|
| 0.8 kg (MeOH)/(l * h) | 370° C. | 1065-1100 | 2 mm | 95.3 | 17.5 | 19.6 | 62.9 |
| N/C = 1.2:1 mol/mol |  | 339-383 | 4 mm | 86.7 | 20.2 | 17.0 | 62.8 |
|  | 380° C. | 935-983 | 4 mm | 91.5 | 17.7 | 17.2 | 65.1 |
|  | 390° C. | 479-527 | 4 mm | 94.8 | 17.3 | 18.6 | 64.0 |
|  | 400° C. | 527-575 | 4 mm | 98.3 | 18.2 | 22.7 | 59.2 |
|  | 410° C. | 695-743 | 4 mm | 98.7 | 19.6 | 24.7 | 55.8 |
|  | 420° C. | 743-791 | 4 mm | 98.8 | 21.0 | 26.4 | 52.6 |
|  | 430° C. | 887-935 | 4 mm | 98.7 | 22.4 | 27.1 | 50.6 |
| 1.2 kg (MeOH)/(l * h) | 380° C. | 1029-1065 | 2 mm | 94.7 | 17.5 | 19.1 | 63.4 |
| N/C = 1.2:1 mol/mol |  | 383-431 | 4 mm | 86.3 | 19.7 | 16.9 | 63.4 |
|  | Rpt. | 983-1031 | 4 mm | 86.4 | 18.8 | 16.6 | 64.6 |
|  | 390° C. | 431-479 | 4 mm | 89.2 | 18.8 | 17.4 | 63.9 |
|  | 400° C. | 575-623 | 4 mm | 92.8 | 17.7 | 18.1 | 64.2 |
|  | 410° C. | 623-695 | 4 mm | 95.8 | 17.3 | 19.9 | 62.8 |
|  | 420° C. | 791-839 | 4 mm | 98.3 | 18.9 | 23.9 | 57.2 |
|  | 430° C. | 839-887 | 4 mm | 98.6 | 20.3 | 25.6 | 54.0 |

TABLE 2

Experimental results for the methylamine synthesis at a molar ratio of 1.8:1

| WHSV, molar ratio | Temperature | Running time, absolute, in h | Diameter of extrudates | Conv (MeOH) | MMA % by weight | DMA % by weight | TMA % by weight |
|---|---|---|---|---|---|---|---|
| 0.4 kg (MeOH)/(l * h) | 350° C. | 935-968 | 2 mm | 90.7 | 24.2 | 18.9 | 56.9 |
| N/C = 1.8:1 mol/mol |  | 1247-1295 | 4 mm | 88.9 | 24.9 | 18.2 | 56.9 |
|  | 360° C. | 793-837 | 2 mm | 95.7 | 23.7 | 21.3 | 55.0 |
|  |  | 1295-1343 | 4 mm | 93.5 | 23.5 | 19.2 | 57.3 |
| 0.8 kg (MeOH)/(l * h) | 360° C. | 758-793 | 2 mm | 86.4 | 25.5 | 18.4 | 56.2 |
| N/C = 1.8:1 mol/mol |  | 0-181 | 4 mm | 81.6 | 27.8 | 18.8 | 53.4 |
|  | Rpt. | 1199-1247 | 4 mm | 82.4 | 26.2 | 18.0 | 55.8 |
|  | 370° C. | 637-757 | 2 mm | 92.7 | 23.7 | 19.7 | 56.6 |
|  |  | 1151-1199 | 4 mm | 88.0 | 24.5 | 18.4 | 57.1 |

TABLE 2-continued

Experimental results for the methylamine synthesis at a molar ratio of 1.8:1

| WHSV, molar ratio | Temperature | Running time, absolute, in h | Diameter of extrudates | Conv (MeOH) | MMA % by weight | DMA % by weight | TMA % by weight |
|---|---|---|---|---|---|---|---|
| | 380° C. | 590-638 | 2 mm | 96.8 | 24.4 | 22.6 | 53.0 |
| | | 181-239 | 4 mm | 90.9 | 24.4 | 21.5 | 54.1 |
| 1.2 kg (MeOH)/(l * h) | 380° C. | 968-993 | 2 mm | 89.8 | 25.0 | 19.5 | 55.5 |
| N/C = 1.8:1 mol/mol | | 239-287 | 4 mm | 85.0 | 26.7 | 19.0 | 54.3 |
| | 385° C. | 993-1029 | 2 mm | 93.2 | 24.5 | 20.7 | 54.7 |
| | | 287-335 | 4 mm | 86.9 | 20.8 | 20.6 | 58.6 |

Rpt. = repeat

The invention claimed is:

1. A shaped body comprising an aluminosilicate and aluminum oxide, wherein the shaped body has a molar Al/Si ratio in the range from 10 to 30 and an at least bimodal pore distribution for pores having a diameter of greater than 1 nm, with the volume of the pores of the shaped body having a diameter of greater than 10 nm corresponding to at least 40% of the total pore volume of the shaped body.

2. The shaped body according to claim 1 which has a molar Al/Si ratio in the range from 11 to 26.

3. The shaped body according to claim 1 which has a bimodal pore distribution for pores having a diameter of greater than 1 nm.

4. The shaped body according to claim 1, wherein the volume of the pores of the shaped body having a diameter of greater than 10 nm corresponds to at least 50% of the total pore volume of the shaped body.

5. The shaped body according to claim 1 which has a BET surface area of $\geq 50$ m$^2$/g.

6. The shaped body according to claim 1 which has a BET surface area in the range from 100 to 250 m$^2$/g.

7. The shaped body according to claim 1 which comprises from 0.01 to 1.75% by weight of sodium, from 0.01 to 1.75% by weight of potassium, from 0.01 to 0.35% by weight of titanium and from 0.01 to 0.35% by weight of iron, in each case based on the total weight.

8. The shaped body according to claim 1 which is an extrudate having a length:diameter ratio of $\geq 1$.

9. The shaped body according to claim 1 which has a cutting hardness of $\geq 10$ newton (N).

10. The shaped body according to claim 1, wherein the aluminosilicate is a clay.

11. The shaped body according to claim 1, wherein the aluminosilicate is a kaolin.

12. The shaped body according to claim 1, wherein the aluminosilicate is kaolinite.

13. The shaped body according to claim 1, wherein the aluminum oxide is gamma-Al$_2$O$_3$.

14. The shaped body according to claim 13, wherein aluminum hydroxide or aluminum oxide/hydroxide (boehmite) is used as precursor for the gamma-aluminum oxide.

15. The shaped body according to claim 1, wherein the proportion of aluminum oxide in the shaped body is $\geq 50\%$ by weight.

16. A process for producing a shaped body according to claim 1, comprising
    (I) preparation of a mixture comprising the aluminosilicate, the aluminum oxide as binder, a pasting agent and a solvent,
    (II) mixing and densification of the mixture,
    (III) shaping of the densified mixture to give a shaped body,
    (IV) drying of the shaped body and
    (V) calcination of the dried shaped body.

17. The process according to claim 16, wherein the mixture contains a pore former in (I).

18. The process according to claim 16, wherein the proportion of aluminosilicate in (I) is chosen in a way, that it is between 1 and 30 wt.-% in the finished shaped body.

19. The process according to claim 16, wherein the proportion of aluminum oxide in (I) is chosen in a way, that it is at least 50 wt.-% in the finished shaped body.

20. The process according to claim 16, wherein shaping in (III) is carried out by extrusion.

21. The process according to claim 16, wherein the calcination in (V) is carried out at a temperature in the range from 350 to 750° C. for a time in the range from 1 to 24 hours.

22. A process for the continuous preparation of methylamines by reaction of methanol or dimethyl ether with ammonia in the presence of a heterogeneous catalyst, wherein shaped bodies according to claim 1 are used as catalyst.

23. The process according to claim 22, wherein the feed stream comprises methanol or dimethyl ether and ammonia together with at least one compound selected from monomethylamine, dimethylamine and trimethylamine.

24. The process according to claim 22, wherein the molar N/C ratio in the feed mixture is in the range from 0.6 to 4.0.

25. The process according to claim 22, wherein the reaction temperature is in the range from 250 to 500° C.

26. The process according to claim 22, wherein the absolute pressure is in the range from 5 to 50 bar.

27. The process according to claim 22, wherein the space velocity over the catalyst, expressed as mass of carbon-comprising compounds in the feed, calculated as methanol, per catalyst volume and time, is in the range from 0.1 to 2.0 kg/l/h.

28. The process according to claim 22 wherein the shaped bodies used as catalyst form a fixed bed comprising two, three, four or more different types of shaped bodies which differ in terms of their acidity.

29. The process according to claim 28, wherein the shaped bodies used as catalyst form a fixed bed comprising two different types of shaped bodies located in separate zones.

30. The process according to claim 29, wherein the difference between the molar Al/Si ratio of the two types of shaped bodies is in the range from 2 to 20.

31. The process according to claim 22, wherein regeneration of the used catalyst is carried out by targeted burning-off of the deposits responsible for deactivation.

* * * * *